United States Patent [19]

Neef et al.

[11] Patent Number: 4,536,401
[45] Date of Patent: Aug. 20, 1985

[54] 11β-ARYL ESTRADIENES, PROCESSES FOR THEIR PRODUCTION AND PHARMACEUTICAL PREPARATIONS CONTAINING THEM

[75] Inventors: Guenter Neef; Gerhard Sauer; Rudolf Wiechert; Helmut Hofmeister; Ralph Rohde; Klaus Annen; Henry Laurent; Sybille Beier; Wolfgang Losert; Walter Elger; David Henderson, all of Berlin, Fed. Rep. of Germany

[73] Assignee: Schering Aktiengesellschaft, Berlin and Bergkamen, Fed. Rep. of Germany

[21] Appl. No.: 581,853

[22] Filed: Feb. 21, 1984

[30] Foreign Application Priority Data

Feb. 18, 1983 [DE] Fed. Rep. of Germany ....... 3306121
Feb. 18, 1983 [DE] Fed. Rep. of Germany ....... 3306124

[51] Int. Cl.³ .............................................. A61K 31/58
[52] U.S. Cl. ................................. 514/173; 260/239.57; 260/239.5; 260/397.45; 548/216; 548/122; 549/31; 514/179
[58] Field of Search ....................... 424/241, 243, 238; 260/239.5, 239.57, 397.1, 397.45; 549/31; 548/122, 216

[56] References Cited

U.S. PATENT DOCUMENTS 4,257,948 3/1981 Costerousse et al. ........... 260/397.45
4,386,085 5/1983 Teutsch et al. ................. 260/397.45

FOREIGN PATENT DOCUMENTS 0005100 7/1981 European Pat. Off. ....... 260/397.45

OTHER PUBLICATIONS

Chem. Abst. 101 (9) Par. 73009y (1984).

Primary Examiner—Elbert L. Roberts
Attorney, Agent, or Firm—Millen & White

[57] ABSTRACT

Compounds of the formula I

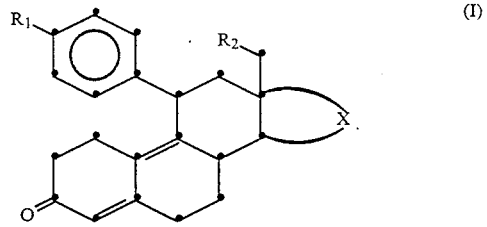

wherein $R^I$ and $R^{II}$ each independently is alkyl of 1-4 carbon atoms, or $R^I$ and $R^{II}$ together with the connecting N-atom form a 5- or 6-membered heterocyclic ring whose remaining atoms are all C-atoms, or which also includes and additional N-atom, an additional O or S atom or a combination thereof;

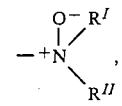

wherein $R^I$ and $R^{II}$ are as defined above;
—$SR^{III}$, wherein $R^{III}$ is methyl, ethyl or phenyl; or
—$OR^{IV}$, wherein $R^{IV}$ is methyl, ethyl, propyl, methoxymethyl, allyl, or β-dimethylaminoethyl;

$R_2$ is hydrogen, methyl, or ethyl;

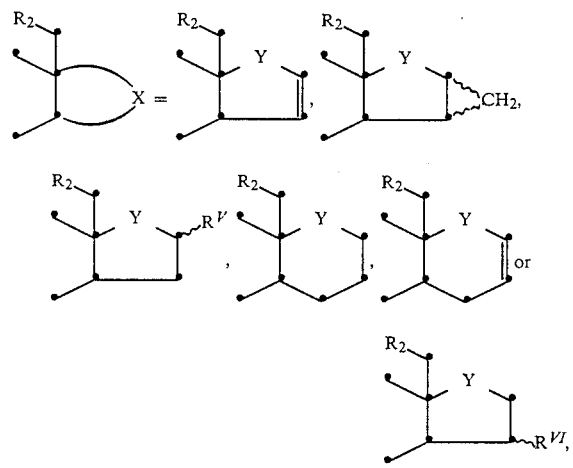

wherein the wavy lines mean that the substituent is in the α- or β-position, and

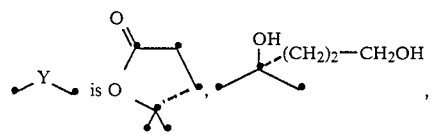

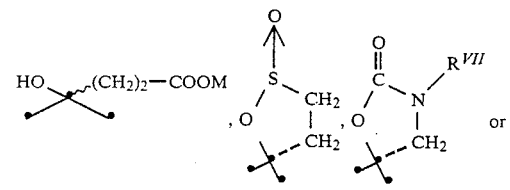

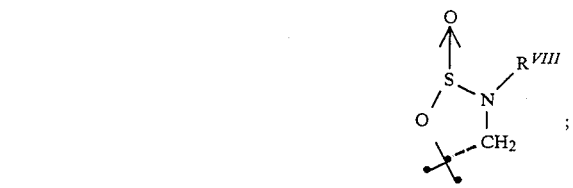

M is Na, K or Li; and $R^V$, $R^{VI}$, $R^{VII}$ and $R^{VIII}$ each independently is alkyl of 1-4 carbon atoms, have valuable pharmacological properties, e.g., a combination of antiprogestational and antimineralocorticordal effects.

26 Claims, No Drawings

11β-ARYL ESTRADIENES, PROCESSES FOR THEIR PRODUCTION AND PHARMACEUTICAL PREPARATIONS CONTAINING THEM

BACKGROUND OF THE INVENTION

The present invention relates to novel 11β-aryl estradienes, a process for their production, and pharmaceutical preparations containing them.

Some 11β-aryl steroids are known. For example, 11β-aryl-17α-propynyl- and -ethynyl-4,9(10)-estradienes are described in European Patent Application No. 82400025.1 (Publication No. 0057115) as compounds exhibiting antiprogestational and antiglucocorticoid activity.

SUMMARY OF THE INVENTION

It is an object of this invention to provide new compounds having valuable pharmacological activity.

Upon further study of the specification and appended claims, further objects and advantages of this invention will become apparent to those skilled in the art.

These objects have been attained by providing 11-aryl estradienes of Formula I

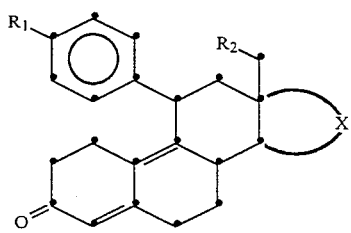
(I)

wherein
$R_1$ is to

wherein $R^I$ and $R^{II}$ each independently is alkyl of 1-4 carbon atoms or $R^I$ and $R^{II}$ together with the connecting N-atom form a 5- or 6-membered heterocyclic ring, all other atoms being C-atoms or, in addition to the connecting N-atom and a second optional N-atom, also an optional O- or S-atom; and the corresponding N-oxides

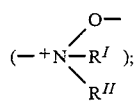

—$SR^{III}$, wherein $R^{III}$ is methyl, ethyl, or phenyl; or —$OR^{IV}$, wherein $R^{IV}$ is methyl, ethyl, propyl, methoxymethyl, allyl, or β-dimethylaminoethyl; $R^2$ is hydrogen, methyl, or ethyl, and

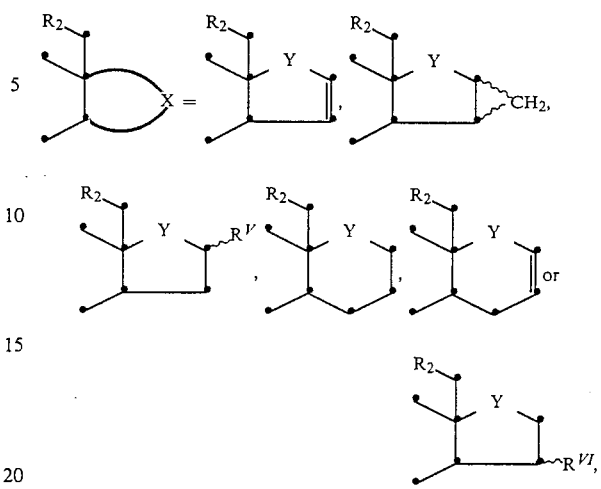

wherein the wavy lines indicate that the substituent is in the α- or β-position, and

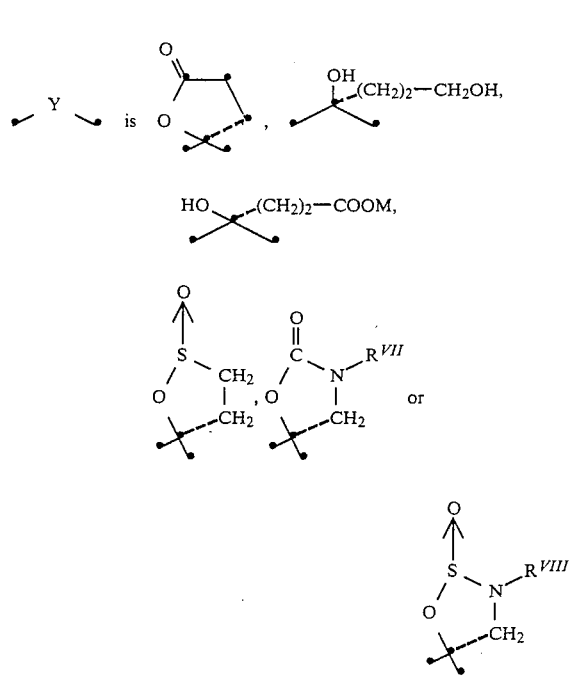

M is Na, K or Li; and $R^V$, $R^{VI}$, $R^{VII}$ and $R^{VIII}$ each independently is alkyl of 1–4 carbon atoms.

DETAILED DISCUSSION

In the compounds of Formula I, the aryl residue in the 11β-position of the steroid skeleton is phenyl substituted by $R_1$ in the para position. When $R_1$ is

then $R^I$ and $R^{II}$ can be alkyl of 1-4 carbon atoms, methyl and ethyl being preferred.

also can represent a heterocyclic five- or six-membered ring which can contain, besides the connecting N-atom and an optional second N-atom, also additionally an O or S atom the remainder being C-atoms; examples include pyrrolidino, piperidino, piperazino, morpholino, oxa-, and thia-zolidino as well as thiadiazolidino rings. Also,

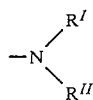

includes the corresponding N-oxides, e.g., dimethylamino-N-oxide, pyrrolidino-, piperidino-, piperazino-, etc., -N-oxide.

In Formula I, $R^V$, $R^{VI}$, $R^{VII}$, and $R^{VIII}$ each is an alkyl residue of 1–4 carbon atoms, preferably methyl or ethyl. In all cases, $C_{1-4}$-alkyl includes methyl, ethyl, n-propyl, isopropyl, n-butyl, isobutyl, sec-butyl, tert-butyl.

It has now been discovered that the novel compounds of Formula I possess antiprogestational and antimineralocorticoid activities. The simultaneous occurrence of antiprogestational and antimineralocorticoid effects in one compound has not heretofore been disclosed. Surprisingly, the two effects occur in the novel compounds even upon oral administration and with a strength of effectiveness comparable to compounds of the state of the art having one of the activities. The relative strengths of the two activities in any given compound of this invention will vary from compound to compound. The antiprogestational effect predominates sometimes, and in other compounds of this invention, the antimineralocorticoid effect is predominant. In all cases, the strength of the two activities can be routinely determined using fully conventional protocols, e.g., as described herein. The novel compounds of Formula I are thus suitable for fertility control as well as for the treatment of diseases accompanied by hyperaldosteronism.

The antimineralocorticoid activity was determined in the antialdosterone test. In this test, adrenalectomized, fasting rats, substituted with fluocortolone and fluocortolone caproate, were treated with 1.0-2.0-4.0 mg of test compound per animal. The test compound was orally administered as a crystalline suspension in NaCl/'-'Myrj"53. One hour after administration, the animals received an intravenous long-term infusion of physiological NaCl solution with an addition of 0.15 μg of aldosterone per animal per hour. Excretion of Na and K salts was measured hourly from the third to the tenth hour, and the Na/K quotient as well as the quotient log Na(100)/K were determined.

The test compounds employed were 11β-(4-dimethylaminophenyl)-17β-hydroxy-17α-(3-hydroxypropyl)-4,9(10)-estradien-3-one (A) of this invention, and the conventional spironolactone (B).

The following Table 1 contains a compilation of the Na/K and log Na(100)/K quotients, as well as the relative antialdosterone effects (RE) of A, based on B=1.

TABLE 1

| | Antialdosterone Test | | | | | | | | | | | | |
|---|---|---|---|---|---|---|---|---|---|---|---|---|---|
| | Na/K | | | | | | | log Na (100)/K | | | | | |
| | A (mg) | | | B (mg) | | | | A (mg) | | | B (mg) | | |
| Hr. | 1.0 | 2.0 | 4.0 | 1.0 | 2.0 | 4.0 | RE | 1.0 | 2.0 | 4.0 | 1.0 | 2.0 | 4.0 | RE |
| 3. | 2.33 | 5.66 | 6.54 | 3.30 | 5.39 | 6.23 | 0.95 | 2.30 | 2.70 | 2.71 | 2.49 | 2.70 | 2.71 | 0.76 |
| 4. | 0.91 | 2.86 | 4.19 | 1.73 | 2.19 | 4.53 | 0.91 | 1.90 | 2.42 | 2.53 | 2.04 | 2.26 | 2.49 | 1.04 |
| 5. | 0.82 | 2.11 | 3.21 | 0.99 | 1.69 | 3.37 | 1.02 | 1.82 | 2.28 | 2.37 | 1.83 | 2.13 | 2.34 | 1.17 |
| 6. | 0.76 | 1.79 | 3.14 | 0.94 | 1.65 | 3.31 | 0.96 | 1.73 | 2.18 | 2.37 | 1.75 | 2.08 | 2.31 | 1.12 |
| 7. | 0.89 | 1.55 | 3.31 | 0.84 | 1.57 | 3.64 | 0.95 | 1.89 | 2.16 | 2.39 | 1.76 | 2.06 | 2.37 | 1.22 |
| 8. | 0.84 | 1.02 | 3.50 | 0.51 | 1.11 | 3.37 | 1.07 | 1.77 | 1.94 | 2.37 | 1.50 | 1.89 | 2.34 | 1.27 |
| 9. | 0.82 | 0.96 | 3.87 | 0.65 | 0.97 | 3.33 | 1.07 | 1.81 | 1.93 | 2.37 | 1.57 | 1.80 | 2.33 | 1.29 |
| 10. | 0.96 | 1.09 | 2.84 | 0.40 | 1.08 | 2.63 | 1.16 | 1.89 | 1.96 | 2.30 | 1.45 | 1.85 | 2.21 | 1.60 |

These results demonstrate the compound A of this invention has approximately the same activity as spironolactone.

In order to characterize the antiprogestational activity, the abortive effect was determined. The tests were conducted on female rats weighing about 200 g. After mating was completed, the start of pregnancy was secured by detection of spermatozoa in vaginal smears. The day of detection of spermatozoa is considered day one of gravidity (=d1 p.c.=day 1 post coitum).

The treatment of the animals with the respective compound to be tested and/or with the solvent took place after nidation of the blastocysts from d5 p.c. to d7 p.c. On d9 p.c., the animals were sacrificed and the uteri examined for implants and resorption sites. Photographs were made of all uteri. The lack of implants was considered in abortion.

The test compounds were dissolved in a benzyl benzoate-castor oil mixture (ratio 1+9). The volume of the vehicle per individual dose was 0.2 ml. Treatment took place subcutaneously.

The test compounds employed were compound A of this invention and 11β-(4-dimethylaminophenyl)-17β-hydroxy-17α-(propyn-1-yl)-4,9(10)-estradien-3-one (C), disclosed in European Patent Application No. 82 400 025.1.

TABLE 2

| Abortion Test Conducted on Gravid Rats | | |
|---|---|---|
| Compound | Dose mg/animal/day s.c. | n Abortion Positive/n Total |
| A | 10.0 | 4/4 |
| | 3.0 | 4/4 |
| | 1.0 | 0/4 |
| C | 3.0 | 4/4 |
| | 1.0 | 2/4 |
| | 0.3 | 0/4 |

It can be seen from Table 2 that compound A of this invention, as well as the conventional compound C are fully effective abortively at a dose of 3.0 mg.

The compounds of this invention, as contrasted with the conventional compound C, do not possess any appreciable antiglucocorticoid side effect, but rather exhibit an antimineralocorticoid effect, e.g., a side effect where the compounds are considered antiprogestational agents. An antimineralocorticoid side effect is harmless in the use of the compounds of this invention as antiprogestational agents, e.g., for elimination of pregnancies and/or for the premature triggering of menstruation, and in cases of hyperaldosteronism is, of course, desirable.

A primary field of usage of the compounds of Formula I is also the treatment of specific types of aldosteronism, hypertension, edemas, and other disturbances caused by aldosterone.

The present invention thus concerns pharmaceutical preparations which contain compounds of Formula I. The pharmacologically effective compounds of this invention can be processed by conventional methods of galenic pharmacy into pharmaceutical preparations for oral or parenteral administration, e.g., to mammals including humans. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositiroes or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 10-100 mg in a pharmaceutically acceptable carrier per unit dosage. The dosage of the compounds according to this invention generally is 10-1000 mg/day when administered to patients, e.g., humans, preferably 50-500 mg/day to achieve an antimineralocorticoid effect analogous to spironolactone and 20-200 mg/day to induce abortions or trigger menstruation analogous to the known agent RU 486.

Suitable dosages and regimens for a given host can be determined using conventional considerations, e.g., by customary comparison of the differential activities of the subject compound and of a known agent, e.g., by means of an appropriate, conventional pharmacological protocol.

The novel compounds of Formula I can be prepared in accordance with this invention by a process for the preparation of 11β-aryl estradienes of Formula I comprising reacting a compound of Formula II

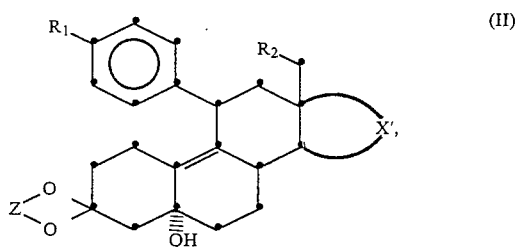

wherein $R_1$ and $R_2$ are as defined in Formukla I, Z is ethylene or 2,2-dimethylpropylene and, when X' is the same as X in Formula I and Y is

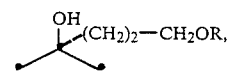

R being a hydrogen atom or a conventional group that can readily be split off, with a dilute acid or an acidic ion exchanger at temperatures of 0°–100° C. in order to produce compounds of Formula I wherein

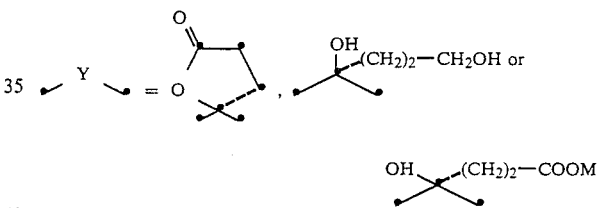

with M=K, Na or Li, and, optionally, conventionally oxidizing the thus-obtained 17α-(3-hydroxypropyl) compound of Formula I to the 17α-propionic acid lactone, and optionally opening the lactone ring with an alkali to obtain the corresponding 17α-propionic acid alkali metal salt; and, when X' is the same as X in Formula I, and Y is

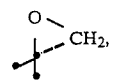

(a) to prepare compounds of Formula I

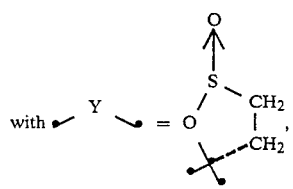

with tert-butylmethyl sulfoxide and alkyl lithium in tetrahydrofuran, then with dilute acid, and subsequently with N-chloro- or N-bromosuccinimide;

(b) to prepare compounds of Formula I with 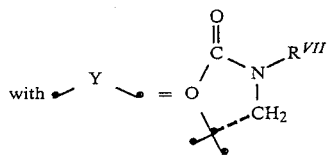

with alkyl amine in the presence of an acid, then with carbonic acid dialkyl ester in the presence of a base, and subsequently with a dilute acid, or with N-alkyl urethane and potassium tert-butylate in hexamethylphosphoric triamide and then with a dilute acid; and (c) to prepare compounds of Formula I with 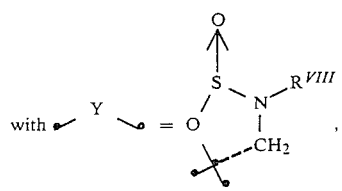, with alkyl amine in the presence of an acid, then with thionyl chloride in triethylamine, and subsequently with a dilute acid.

Starting with the 17α-oxypropyl-17β-hydroxy compounds of Formula II, a treatment is carried out with an acid or with an acidic ion exchanger to split off water to form the 4(5)-double bond and simultaneously perform a ketal cleavage and removal of any additional blocking groups that are present and can be split off with the acid.

The acid treatment takes place conventionally by dissolving the compound of Formula II containing a 3-ketal group and a 5α-hydroxy group and an optionally O-blocked 17α-(3-hydroxypropyl) group, in a water-miscible solvent, such as aqueous methanol, ethanol, or acetone, and treating the solution with catalytic amounts of a mineral or sulfonic acid, e.g., hydrochloric acid, sulfuric acid, phosphoric acid, perchloric acid, or p-toluene-sulfonic acid, or with an organic acid, such as acetic acid, until water has been split off and the blocking groups have been eliminated. The reaction, taking place at a temperature of 0°–100° C., can also be carried out with an acidic ion exchanger. The course of the reaction can be conventionally controlled with analytical methods, for example by thin-layer chromatography of withdrawn samples.

If final products of Formula I are desired wherein Y is

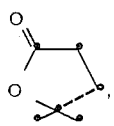, then the 17α-(3-hydroxypropyl) compounds (Y = 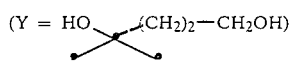)

are conventionally oxidized. The conditions during oxidation are dependent on the nature of the substituent $R_1$ in Formula I. A person skilled in the art will routinely decide from case to case which of the known methods is suitable and which unsuitable. If $R_1$ is a dialkylamino or alkylthio residue, for example, chromic acid reagents are unsuitable for oxidation since these primarily attack the dialkylamino or alkylthio group. In these instances, oxidizing agents must be employed such a silver carbonate/"Celite" (Fetizon reagent; M. Fetizon and M. Golfier, Compt. rend. 267:900 [1968]) or platinum/oxygen (H. Muxfeldt et al., Angewandte Chemie, Int. Ed. 1:157 [1962]). In contrast, if $R_1$ is an alkoxy group, then it is possible also to use oxidizing agents such as Jones' reagent, chromic acid-pyridine, pyridinium dichromate, or pyridinium chlorochromate.

If final products of Formula I are desired wherein Y is

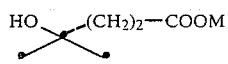

wherein M = alkali metal, then the 17-spirolactones (Y = O 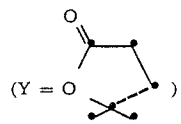)

are likewise reacted in a manner known per se. For this purpose, the lactone can be treated with dilute alkaline solution, thus forming the alkali salt of 17α-propionic acid. Alkali salts include potassium, sodium, or lithium salts, the potassium salt being preferred.

Starting with the oxiranes of Formula II, prepared conventionally from the corresponding 17-ketones with trimethylsulfonium iodide, there is formed first of all the 17-spiro hererocycle according to (b) and (c); according to (a), a precursor of the heterocycle, [21-(1,1-dimethylsulfinyl)], is first formed.

According to (a), the reaction of the compound of Formula II with tert-butylmethyl sulfoxide and alkyl lithium takes place in tetrahydrofuran. Suitable alkyl lithiums include, for example, methyl-and n-butyllithium.

According to (b), the compound of Formula II is first heated with an alkylamine, especially methyl- or ethylamine, in the presence of an acid, such a p-toluenesulfonic acid, to 80°–150° C. The resultant 17α-alkylaminomethyl compound is subsequently heated under reflux with a carbonic acid dialkyl ester, especially a dimethyl or diethyl ester, in the presence of a base, such as potassium tert-butylate or alkali propionate or phenylate. According to this method, the [17(β-1')spiro-5']oxazolidin-2-one is obtained while water is simultaneously split off and the 4(5)-double bond is formed.

According to another method, the compound of Formula II is reacted with N-alkyl urethane and potassium tert-butylate in hexamethylphosphoric triamide to form the [17(β-1')spiro-5']oxazolidin-2-one. The reaction takes place at temperatures of about 80° to 150° C. Especially suitable N-alkyl urethanes are N-methylurethane and N-ethylurethane.

According to (c), the compound of Formula II is first heated with an alkylamine, especially methyl- or ethylamine, in the presence of an acid, such a-toluenesulfonic acid, to 80°–150° C. The thus-obtained 17α- alkylaminomethyl compound is subsequently treated at 0°-20° C. with thionyl chloride in the presence of triethylamine, yielding [17(β-1')spiro-5'][1,2,3]oxathiazolidine-2-oxide.

For the subsequent splitting off of water from the 5α-hydroxy compound with formation of the 4(5)-double bond and simultaneous ketal cleavage, a treatment is carried out according to (a), (b), and (c) with an aqueous acid, e.g., aqueous acetic acid, at temperatures of 0°-100° C.

Ring closure to the [17(β-1')spiro-5'][1,2]oxathiolane-2-oxide is accomplished according to (a) by reacting the 21-(1,1-dimethylsulfinyl) compound

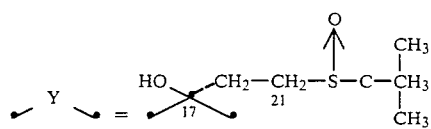

with N-chloro-or N-bromosuccinimide in the presence of water.

The starting compounds of Formula II wherein

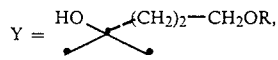

used in the process of this invention, wherein R is a hydrogen atom or a group readily split off in an acidic medium, can be prepared according to known methods. Readily cleavable groups include alkoyxalkyl groups, such as methoxymethyl, ethoxymethyl, or ring-closed ethers, such as tetrahydropyran.

Preparation of the starting compounds of Formula II can be described with reference to the following reaction scheme:

for example with 1-lithium-3-tetrahydropyran-2'-yloxy-propyne-1, to form the 17α-(3-oxygenated-1-propynyl]-17β-hydroxy compounds (2). Introduction of the 11β-aryl residue to form (3) takes place either by Cu(I)-catalyzed Grignard reaction with the corresponding aryl magnesium halides (Tetrahedron Letters 1979: 2051) or by reaction with mixed organocuprates of the type R$_2$Cu(CN)Li$_2$ (J. Am. Chem. Soc. 103: 7672 [1981]). Hydrogenation of (3) to form the the starting compounds (II) must be conducted under conditions ensuring exclusive attack on the C-C-triple bond without saturation of the tetrasubstituted 9(10)-double bond. This can be accomplished, for example, by hydrogenating at room temperature and under normal pressure in a solvent, e.g., methanol, ethanol, propanol, tetrahydrofuran (THF), or ethyl acetate, with the addition of noble metal catalysts, such as platinum or palladium.

The various steroids needed in these reactions are all known or readily preparable using fully conventional techniques The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, etc., or other reactions disclosed herein or otherwise conventional, will be applicable to the preparation of the corresponding compounds of this invention.

Without further elaboration, it is believed that one skilled in the art can, using the preceding description,

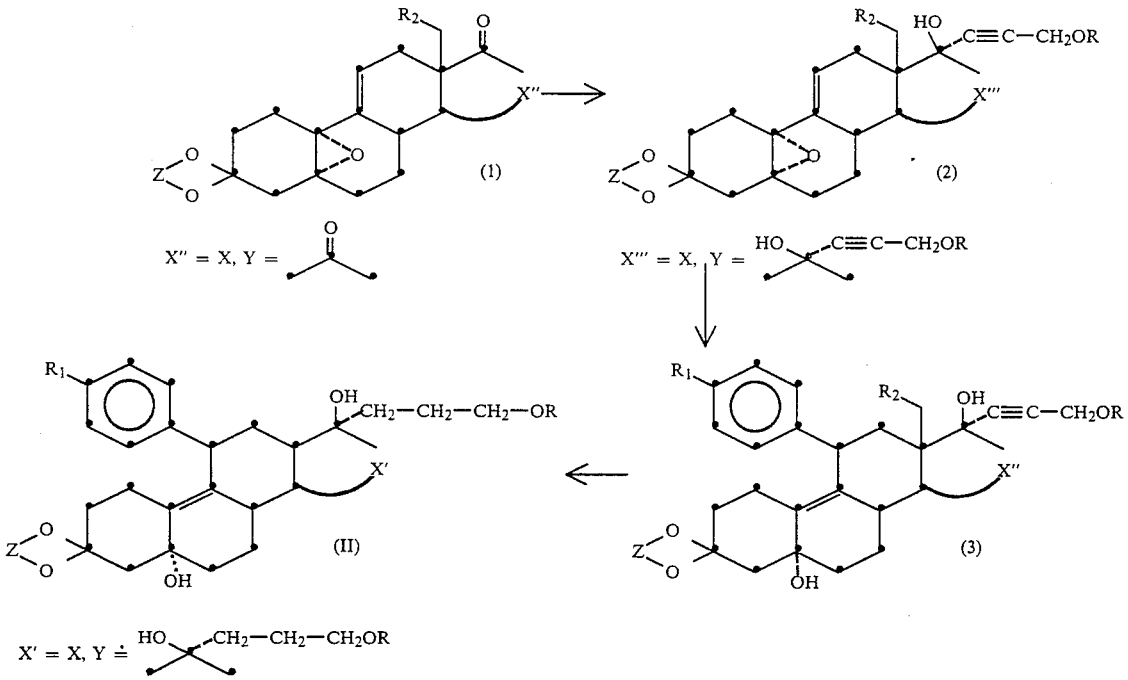

Oxiranes (1) according to European Patent Application No. 82400025.1 (Publication No. 0057115) are reacted with metallized derivatives of propargyl alcohol, utilize the present invention to its fullest extent. The following preferred specific embodiments are, therefore, to be construed as merely illustrative, and not limitative of the remainder of the disclosure in any way whatsoever, In the following examples, all temperatures are set forth uncorrected in degrees Celsius; unless otherwise indicated, all parts and percentages are by weight.

The preparation of several starting compounds of general Formula II will be described in greater detail below:

1(a) Under ice water cooling, 208 ml of a 15% solution of n-butyllithium in hexane is added dropwise to a solution of 35.7 g of 3-tetrahydropyran-2'-yloxy-1-propyne in 760 ml of absolute tetrahydrofuran. After the adding step, the mixture is stirred for another 15 minutes at +5° to +10° C. and then a solution of 23.7 g of 3,3-(2,2-dimethylpropane-1,3-dioxy)-5α,10α-oxido-9(11)-estren-17-one in 470 m. of absolute THF is added dropwise thereto. The mixture is then stirred for 20 minutes at 25° C., whereupon the reaction solution is poured into about 5 l of ice water and extracted with ethyl acetate. The ethyl acetate extract is dried over sodium sulfate/active carbon and concentrated under vacuum. After filtration over aluminum oxide with hexane/ethyl acetate as the eluents, 29.3 g of 3,3-(2,2-dimethylpropane-1,3-dioxy)-5α,10α-oxido-17α-[3-(tetrahydropyran-2-yloxy)-1-propynyl]-9(11)-estren-17β-ol is obtained as a colorless oil.

(b) A suspension of 5.28 g of magnesium (filings) in 275 ml of absolute THF is combined in succession with 0.05 ml of methyl iodide and a solution of 50.27 g of 4-bromodimethylaniline in 245 ml of absolute THF. The mixture is stirred until complete dissolution of the magnesium in an argon atmosphere; in this step, the internal temperature is not to rise above 50° C. Subsequently the mixture is cooled to +5° C., the Grignard solution is combined with 1.12 g of CuCl, and agitated for 15 minutes at +5°–+10° C. Then a solution of 29.3 g of the product obtained in (a) in 275 ml of absolute THF is added dropwise thereto, and the mixture is further stirred for 5 hours at room temperature. The reaction solution is thereafter poured into about 4 l of ice water and extracted with ethyl acetate. Chromatography of the resultant crude product over aluminum oxide with hexane/ethyl acetate yields 32.6 g of 11β-(4-dimethylaminophenyl)-3,3-(2,2-dimethylpropane-1,3-dioxy)-17α-[3-(tetrahydropyran-2-yloxy)-1-propynyl]-9(10)-estrene-5α,17β-diol as a yellowish oil.

(c) A solution of 2.0 g of the product obtained in (b) in 20 ml of ethanol is hydrogenated, after the addition of 120 mg of palladium-carbon (10%) at room temperature and under normal pressure. After 2 hours and with a hydrogen absorption of 141 ml, the product is filtered off from the catalyst and the filtrate is concentrated. The thus-obtained crude product is utilized in Example 1 without further purification.

2(a) According to 1(a), 22.6 g of 3,3-(2,2-dimethylpropane-1,3-dioxy)-18-methyl-5α,10α-oxido-9(11)-estren-17-one (mp 156°–158° C.) is reacted with 1-lithio-3-(tetrahydropyran-2-yloxy)propyne-1, thus obtaining 25.4 g of 3,3-(2,2-dimethylpropane-1,3-dioxy)-18-methyl-5α,10α-oxido-17α-[3-(tetrahydropyran-2-yloxy)-1-propynyl]-9(11)-estren-17β-ol as a colorless oil.

(b) At 25° C., 0.1 ml of methyl iodide, then a solution of 40 g of p-dimethylaminoethoxyphenyl bromide (prepared according to D. Lednicer et al., J. Med. Chem. 8: 52 [1964]) in 200 ml of absolute THF are added dropwise to a suspension of 4.3 g of magnesium (filings) in 40 ml of absolute THF. The mixture is stirred until complete dissolution of the magnesium at a bath temperature of maximally 70° C. After cooling to 0° C., 820 mg of CuCl is added and the mixture is agitated for 20 minutes at 0° C. Then a solution of 15.9 g of the product obtained in (a) in 120 ml of absolute THF is added dropwise thereto. The mixture is stirred for 16 hours at 25° C., poured into ice water, and extracted with ethyl acetate. Chromatography over aluminum oxide (neutral, III) with hexane/ethyl acetate yields 17.1 g of a yellowish oil.

(c) Hydrogenation of 3.4 g of the product obtained in (b) in accordance with 1(c) yields 3.4 g of 11β-[4-(2-dimethylaminoethoxy)phenyl]-3,3-(2,2-dimethylpropane-1,3-dioxy)-18-methyl-17α-[3-(tetrahydropyran-2-yloxy)propyl]-9(10)-estrene-5α,17β-diol.

3(a) As described in 1(b), a Grignard reagent is prepared from 2.4 g of magnesium in 120 ml of absolute THF and 11.6 ml of 4-bromoanisole, and combined with 260 mg of CuCl. A solution of 6.4 g of the adduct prepared in 1(a) in 80 ml of absolute THF is added dropwise at 0° C. The reaction solution is stirred for 4 hours at 25° C. and worked up as described in 1(b), thus obtaining 7.15 g of an oily product.

(b) 7.15 g of the product obtained in (a) is hydrogenated as in 1(c), yielding 7.05 g of a crude product which is utilized in Example 3 without further purification.

4(a) Under the conditions described in 1(a), the organolithium compound is produced from 6.7 g of propargyl tetrahydropyranyl ether in 100 ml of THF and 40 ml of n-butyllithium (15% in hexane), and reacted with 4.63 g of 3,3(2,2-dimethylpropane-1,3-dioxy)-16β-methyl-5α,10α-oxido-9(11)-estren-17-one. Chromatography yields 4.22 g of 3,3-(2,2-dimethylpropane-1,3-dioxy)-16β-methyl-5α,10α-oxido-17α-[3-(tetrahydropyran-2-yloxy)prop-1-ynyl]-9(11)-estren-17β-ol as a crystalline mixture of isomers, mp 156°–166° C.

(b) Under the conditions of 1(b), a Grignard reagent is prepared from 1.23 g of magnesium filings in 100 ml of absolute THF, 11.48 g of 4-dimethylaminophenyl bromide in 50 ml of absolute THF, 0.03 ml of methyl iodide, and 230 mg of CuCl; this reagent is reacted with 3.55 g of 3,3-(2,2-dimethylpropane-1,3-dioxy)-16β-methyl-5α,10α-oxido-17α-(3-tetrahydropyran-2-yloxy-prop-1-ynyl)-9(11)-estren-17β-ol. Chromatography yields 3.56 g of 11β-(4-dimethylaminophenyl)-3,3-(2,2-dimethylpropane-1,3-dioxy)-16β-methyl-17α-[3-(tetrahydropyran-2-yloxy)prop-1-ynyl]-9(10)-estrene-5α,17β-diol as an oily mixture of isomers.

(c) Hydrogenation of 3.56 g of the product from the Grignard reaction under the conditions of 1(c) results in 3.42 g of oily 11β-(4-dimethylaminophenyl)-3,3-(2,2-dimethylpropane-1,3-dioxy)-16β-methyl-17α-[3-(tetrahydropyran-2-yloxy)propyl]-9(10)-estrene-5α,17β-diol.

5(a) A solution of 10.5 g of 4-(2,5-dimethylpyrrol-1-yl)bromobenzene (prepared according to J. Chem. Soc. 1951: 3155) in 40 ml of absolute tetrahydrofuran is added dropwise to a suspension of 1.02 g of magnesium filings and 0.05 ml of methyl iodide in 25 ml of absolute tetrahydrofuran in such a way that the temperature does not exceed 45° C. after onset of reaction. After the magnesium has been dissolved, the mixture is cooled to 0° C., 210 mg of CuCl is added, the mixture is stirred for 15 minutes at 0° C., and finally a solution of 4.00 g of 3,3-(2,2-dimethylpropane-1,3-dioxy)-5α,10α-oxido-17α-[3-(tetrahydropyran-2-yloxy)prop-1-ynyl]-9(11)-estren- 17β-ol in 50 ml of absolute tetrahydrofuran is added dropwise thereto. Subsequently the mixture is agitated overnight at room temperature, poured on ice water, and extracted with ethyl acetate. Chromatography on Al₂O₃ (neutral, III) with hexane/ethyl acetate yields 4.42 g of 3,3-(2,2-dimethylpropane-1,3-dioxy)-11β-[4-(2,5-dimethylpyrrol-1-yl)phenyl]-17α-[3-(tetrahydropyran-2-yloxy)prop-1-ynyl]-9(10)-estrene-5α,17β-diol as a pale-yellow, solid foam.

(b) 4.15 g of the product obtained in (a) is hydrogenated in 50 ml of ethanol with the addition of 400 mg of palladium-carbon (10%) under normal conditions. After absorption of 290 ml of H₂, the mixture is filtered off from the catalyst and concentrated. By chromatography on Al₂O₃ (neutral, III) with hexane/ethyl acetate, 3.37 g of 3,3-(2,2-dimethylpropane-1,3-dioxy)-11β-[4-(2,5-dimethylpyrrol-1-yl)phenyl]-17α-[3-(tetrahydropyran-2-yloxy)propyl]-9(10)-estrene-5α,17β-diol is obtained as a pale-yellow, solid foam.

6(a) 1.46 g of magnesium filings and 0.05 ml of methyl iodide are combined in 15 ml of absolute tetrahydrofuran. Then a solution of 14.5 g of N-(4-bromophenyl)-piperidine (produced according to J. Am. Chem. Soc. 75:5280 [1953]) in 100 ml of absolute tetrahydrofuran is added dropwise thereto in such a way that the temperature does not exceed 45° C. after onset of reaction. After the magnesium has been dissolved, the mixture is cooled to 0° C., 450 mg of CuCl is added, the mixture is agitated for 15 minutes at 0° C. and finally a solution of 6.0 g of 3,3-(2,2-dimethylpropane-1,3-dioxy)-5α,10α-oxido-17α-[3-(tetrahydropyran-2-yloxy)prop-1-ynyl]-9(11)-estren-17β-ol in 50 ml of absolute tetrahydrofuran is added dropwise thereto. The mixture is thereafter agitated overnight at room temperature, poured on ice water, and extracted with ethyl acetate. Chromatography on Al₂O₃ (neutral, III) with hexane/ethyl acetate yields 7.0 g of 3,3-(2,2-dimethylpropane-1,3-dioxy)-11β-(4-piperidinophenyl)-17α-[3-(tetrahydropyran-2-yloxy)prop-1-ynyl]-9(10)-estrene-5α,17β-diol as a colorless, solid foam.

(b) 7.0 g of the product obtained in (a) is hydrogenated in 250 ml of ethanol with the addition of 680 mg of palladium-carbon (10%) under normal conditions. After absorption of 470 ml of H₂, the mixture is filtered off from the catalyst and concentrated, thus obtaining 6.86 g of 3,3-(2,2-dimethylpropane-1,3-dioxy)-11β-(4-piperidinophenyl)-17α-[3-(tetrahydropyran-2-yloxy)-propyl]-9(10)-estrene-5α,17β-diol as a colorless oil which is utilized in the subsequent stage without further purification (Example 8).

7(a) 2.16 g of magnesium filings and 0.05 ml of methyl iodide are combined in 15 ml of absolute tetrahydrofuran. Then a solution of 13.5 g of N-(4-bromophenyl)pyrrolidine (prepared according to J. Am. Chem. Soc. 75:5280 [1953]) in 150 ml of absolute tetrahydrofuran is added dropwise in such a way that the temperature of the reaction mixture does not exceed 45° C. after onset of reaction. After the magnesium has been dissolved, the reaction mixture is cooled to 0° C., 450 mg of CuCl is added, the mixture is stirred for 15 minutes at 0° C. and finally a solution of 6.0 g of 3,3-(2,2-dimethylpropane-1,3-dioxy)-5α,10α-oxido-17α-[3-(tetrahydropyran-2-yloxy)prop-1-ynyl]-9(11)-estren-17β-ol in 70 ml of absolute tetrahydrofuran is added dropwise thereto. The reaction mixture is then agitated overnight at room temperature, poured on ice water, and extracted with ethyl acetate. Chromatography on Al₂O₃ (neutral, III) with hexane/ethyl acetate yields in this way 7.0 g of 3,3-(2,2-dimethylpropane-1,3-dioxy)-11β-[4-(pyrrolidin-1-yl)phenyl]-17α-[3-(tetrahydropyran-2-yloxy)-prop-1-ynyl]-9(10)-estrene-5α,17β-diol as a colorless, solid foam.

(b) A solution of 7.0 g of the product obtained according to (a) in 250 ml of ethanol is hydrogenated after adding 670 mg of palladium-carbon (10%) at room temperature and under normal pressure. After absorption of 470 ml of H₂ the mixture is filtered off from the catalyst; the filtrate is concentrated and chromatographed on Al₂O₃ (neutral, III) with hexane/ethyl acetate, thus obtaining 6.3 g of 3,3-(2,2-dimethylpropane-1,3-dioxy)-11β-[4-(pyrrolidin-1-yl)phenyl]-17α-[3-(tetrahydropyran-2-yloxy)propyl]-9(10)-estrene-5α,17β-diol as a colorless foam.

EXAMPLE 1

3-[11β-(4-Dimethylaminophenyl)-17β-hydroxy-3-oxo-4,9(10)-estradien-17α-yl]propionic Acid Lactone 1.96 g of 11β-(4-dimethylaminophenyl)-3,3-(2,2-dimethylpropane-1,3-dioxy)-17α-[3-(tetrahydropyran-2-yloxy)propyl]-9(10)-estrene-5α,17β-diol is taken up in 19 ml of 70% aqueous acetic acid and stirred for 3 hours at 60° C. The mixture is then poured into ice water, adjusted to a pH of approximately 10 by adding concentrated aqueous NH₃ solution, and extracted with methylene chloride. Filtration of the crude product over silica gel (hexane/ethyl acetate) yields 1.15 g of 11β-(4-dimethylaminophenyl)-17β-hydroxy-17α-(3-hydroxypropyl)-4,9(10)-estradien-3-one as a solid foam. ¹H-NMR (CDCl₃): δ=0.60 ppm (δ, 3H, H-18), 2.92 [δ, 6H, N(CH₃)₂]; 3.71 (m, 2H, CH₂OH); 4.34 (m, 1H, H-11); 5.77 (m, 1H, H-4); 6.66 and 7.00 (AA'BB' system, each 2H, arom. H).

UV (MeOH): λ260 nm (ε=16,900); 304 (19,720).

A solution of 1.0 g of the above product in 150 ml of toluene is heated under reflux for 6 hours after adding 7.45 g of silver carbonate on "Celite" (prepared according to M. Fetizon and M. Golfier, Compt. rend., 267:900 [1968]). After cooling, the reaction mixture is filtered, the filter residue is thoroughly washed out with methylene chloride, and the filtrate is concentrated, thus obtaining 730 mg of the lactone as an amorphous solid.

NMR (CDCl₃): δ=0.68 ppm (S, 3H, H-18); 2.96 [s, 6H, N(CH₃)₂]; 4.42 (m, 1H, H-11); 5.81 (m, 1H, H-4); 6.69 and 7.02 (AA'BB'-, each 2H, arom. H).

EXAMPLE 2

3-[11β-[4-(2-Dimethylaminoethoxy)phenyl]-17β-hydroxy-18-methyl-3-oxo-4,9(10)-estradien-17α-yl]-propionic Acid Lactone A solution of 3.4 g of 11β-[4-(2-dimethylaminoethoxyphenyl]-3,3-(2,2-dimethylpropane-1,3-dioxy)-18-methyl-17α-[3-(tetrahydropyran-2-yloxy)propyl]-9(10)-estrene-5α,17β-diol in 120 ml of 90% aqueous ethanol is heated after adding 1.75 g of p-toluenesulfonic acid for 15 minutes under reflux. After cooling, the mixture is poured into ice water, adjusted to pH 10.5 by addition of NH₃ solution, and extracted with methylene chloride. Chromatography over silica gel with hexane/ethyl acetate yields 1.86 g of 11β-[4-(2-dimethylaminoethoxy)phenyl]-17β-hydroxy-17α-(3-hydroxypropyl)-18-methyl-4,9(10)-estradien-3-one as a solid foam. ¹H-NMR (CDCl₃): δ=0.32 ppm (t, 3H, CH₂-CH₃); 2.32 [s, 6H, N(CH₃)₂]; 2.70 (t, 2H, CH₂-CH₂-N); 4.01 (t, 2H, CH₂-CH₂-O); 4.36 (m, 1H, H-11); 5.74 (m, 1H, H-4).

UV (methanol): λ$_{max}$ 282 (10, 400); 289 (13,600); 306 nm (ε = 18,720).

Oxidation of 1.6 g of the above product under the conditions of Example 1 (second paragraph) yields 1.3 g of the lactone as a yellowish, amorphous glass. IR (CHCl$_3$): 1730 cm$^{-1}$ (lactone carbonyl); 1685 (C=O).

EXAMPLE 3

3-[17β-Hydroxy-11β-(4-methoxyphenyl)-3-oxo-4,9(10)-estradien-17α-yl]propionic Acid Lactone A solution of 7.05 g of 3,3-(2,2-dimethylpropane-1,3-dioxy)-11β-(4-methoxyphenyl)-17α-[3-(tetrahydropyran-2-yloxy)propyl]-9(10)-estrene-5α,17α-diol is stirred in 50 ml of 70% aqueous acetic acid for 2 hours at 60° C. After cooling, the mixture is poured into water and the acidic, aqueous solution is extracted with methylene chloride. Chromatography of the resultant crude product over silica gel with hexane/ethyl acetate yields 3.8 g of 17β-hydroxy-17α-(3-hydroxypropyl)-11β-(4-methoxyphenyl)-4,9(10)-estradien-3-one as a yellowish foam.

$^1$H-NMR (CDCl$_3$): δ = 0.56 ppm (s, 3H, H-18); 3.76 (s, 3H, OCH$_3$); 4.33 (m, 1H, H-11); 5.71 (m, 1H, H-4); 6.74 and 7.03 (AA'BB', each 2H, arom. H).

A solution of 2.5 g of the above-obtained product in 150 ml of methylene chloride is combined at room temperature with 3.3 g of pyridinium chlorochromate in incremental portions and then stirred for 2 hours at 25° C. Then the mixture is filtered over "Celite", the filtrate is washed first with NaHCO$_3$ solution, then with saturated NH$_4$Cl solution, dried over sodium sulfate/active carbon, and concentrated. Column chromatography over silica gel with hexane/ethyl acetate yields 1.45 g of the lactone.

$^1$H-NMR (CDCl$_3$): δ = 0.62 ppm (s, 3H, H-18); 3.77 (s, 3H, OCH$_3$); 4.40 (m, 1H, H-11); 5.77 (s, 1H, H-4); 6.91 (AA'BB', 4H, arom. H).

EXAMPLE 4

11β-(4-Dimethylaminophenyl)-17β-hydroxy-17α-(3-hydroxypropyl)-16β-methyl-4,9(10)-estradien-3-one Cleavage of 3.42 g of 11β-(4-dimethylaminophenyl)-3,3-(2,2-dimethylpropane-1,3-dioxy)-16β-methyl-17α-[3-(tetrahydropyran-2-yloxy)propyl]-9(10)-estrene-5α,17β-diol with 60 ml of 70% aqueous acetic acid under the conditions of Example 1 produces 1.97 g of 11β-(4-dimethylaminophenyl)-17β-hydroxy-17α-(3-hydroxypropyl)-16β-methyl-4,9(10)-estradien-3-one as a yellowish oil.

$^1$H-NMR (CDCl$_3$): δ = 0.51 ppm (s, 3H, H-18); 0.96 [d (J = 7 Hz), 3H, 16β-CH$_3$]; 2.88 [s, 6H, N(CH$_3$)$_2$]; 3.63 (m, 2H, CH$_2$OH); 4.32 (m, 1H, H-11); 5.73 (s, 1H, H-4); 6.60 and 6.98 (AA'BB', each 2H, arom. H).

EXAMPLE 5

11β-(4-Dimethylaminophenyl)-17aβ-hydroxy-17aα-(3-hydroxypropyl)-D-homo-4,9(10)-estradien-3-one After conducting the reaction sequence 1(a)-(d) [1(d) = Example 1], 1.43 g of 3,3-(2,2-dimethylpropane-1,3-dioxy)-5α,10α-oxido-D-homo-9(11)-estren-17a-one yields, without purification of the intermediate stages, 630 mg of 11β-(4-dimethylaminophenyl)-17aβ-hydroxy-17aα-(3-hydroxypropyl)-D-homo-4,9(10)-estradien-3-one as a yellowish foam.

$^1$H-NMR (CDCl$_3$): δ = 0.58 ppm (s, 3H, H-18); 2.97 [s, 6H, N(CH$_3$)$_2$]; 4.36 (m, 1H, H-11); 5.74 (s, 1H, H-4); 6.63 and 6.69 (AA'BB', each 2H, arom. H).

EXAMPLE 6

11β-(4-Dimethylaminophenyl)-17β-hydroxy-17α-(3-hydroxypropyl)-18-methyl-4,9(10)-estradien-3-one 4.32 g of 3,3-(2,2-dimethylpropane-1,3-dioxy)-18-methyl-5α,10α-oxido-17α-[3-(tetrahydropyran-2-yloxy)prop-1-ynyl]-9(11)-estren-17β-ol, prepared as described in 2(a), yields, after reaction under the conditions of 1(b)-(d) [1(d) = Example 1], 225 g of 11β-(4-dimethylaminophenyl)-17β-hydroxy-17α-(3-hydroxypropyl)-18-methyl-4,9(10)-estradien-3-one as a light-yellow oil.

$^1$H-NMR (CDCl$_3$): δ = 0.32 ppm [t (J = 7 Hz), 3H, 13-CH$_2$-CHHD 3]; 2.90 [s, 6H, N(CH$_3$)$_2$]; 3.68 (m, 2H, CH$_2$OH); 4.31 (m, 1H, H-11); 5.72 (s, 1H, H-4); 6.63 and 7.03 (AA'BB', each 2H, arom. H).

UV (methanol): λ$_{max}$ 260 nm (ε = 17-090); 307 (ε = 19,500).

EXAMPLE 7

11β-[4-(2,5-Dimethylpyrrol-1-yl)phenyl]-17β-hydroxy-17α-(3-hydroxypropyl)-4,9(10)-extradien-3-one A solution of 0.98 g of 3,3-(2,2-dimethylpropane-1,3-dioxy)-11β-[4-(2,5-dimethylpyrrol-1-yl)phenyl]-17α-[3-(tetrahydropyran-2yloxy)propyl]-9(10)-estrene-5α,17β-diol and 100 mg of p-toluenesulfonic acid monohydrate in 30 ml of ethanol is stirred for 2 hours at room temperature. The reaction mixture is then poured on a mixture of 10 ml of concentrated ammonia solution and 50 g of ice and extracted with ethyl acetate. Chromatography on Al$_2$O$_3$ (neutral, III) with hexane/ethyl acetate yields 0.36 g of 11β-[4-(2,5-dimethylpyrrol-1-yl)phenyl]-17β-hydroxy-17α-(3-hydroxypropyl)-4,9(10)-estradien-3-one as a lemon-yellow, solid foam.

EXAMPLE 8

17β-Hydroxy-17α-(3-hydroxypropyl)-11β-(4-piperidinophenyl)-4,9(10)-estradien-3-one A solution of 6.86 g of 3,3-(2,2-dimethylpropane-1,3-dioxy)-11β-(4-piperidinophenyl)-17α-[3-(tetrahydropyran-2-yloxy)propyl]-9(10)-estrene-5α,17β-diol in 150 ml of 70% acetic acid is stirred overnight at room temperature and then for one hour at 50° C. After cooling, the mixture is poured on a mixture of 30 ml of concentrated ammonia solution and 100 g of ice and extracted with ethyl acetate. Chromatography on silica gel yields 4.1 g of 17β-hydroxyu-17α-(3-hydroxypropyl)-11β-(4-piperidinophenyl)-4,9(10)-estradien-3-one as a lemon-yellow, solid foam.

EXAMPLE 9

17β-Hydroxy-17α-(3-hydroxypropyl)-11β-[4-(pyrrolidin-1-yl)phenyl]-4,9(10)-estradien-3-one A solution of 6.3 g of 3,3-(2,2-dimethylpropane-1,3-dioxy)-11β-[4-pyrrolidin-1-yl)phenyl]-17α-[3-(tetrahydropyran-2-yloxy)propyl]-9(10)-estrene-5α,17β-diol in 150 ml of 70% acetic acid is stirred overnight at room temperature. Then the mixture is heated for one hour to 50° C. After cooling, the solution is poured on a mixture of 30 ml of concentrated ammonia solution and 100 g of ice and extracted with ethyl acetate. Chromatography on SiO$_2$ yields 3.5 g of 17β-hydroxy-17α-(hydroxypropyl)-11β-[4-(pyrrolidin-1-yl)phenyl]-4,9(10)-estradien-3-one as a lemon-yellow, solid foam.

EXAMPLE 10

Under argon, 2.3 g of potassium tert-butylate is added in incremental portions at room temperature to a suspension of 3.6 g of 11β-(4-dimethylaminophenyl)-3,3-ethylenedioxy -5α-hydroxy-9-estren-17-one and 3.3 g of trimethylsulfonium iodide in 38 ml of dimethylformamide within 10 minutes. After 30 minutes, the mixture is stirred into ice/water. The thus-precipitated product is suctioned off, washed with water, dissolved in ethyl acetate, and dried over sodium sulfate. Chromatography on silica gel with acetone/hexane produces 3.1 g of 11β-(4-dimethylaminophenyl)-3,3-ethylenedioxy-9-estrene[17(β-1')spiro-3']oxiran-5α-ol, mp 128.0° C. (with decomposition).

EXAMPLE 11

Analogously to Example 10, 1.2 g of 3,3-ethylenedioxy-5α-hydroxy-11β-(4-methoxyphenyl)-9-estren-17-one is reacted with trimethylsulfonium iodide and potassium tert-butylate in dimethylformamide. After chromatography on silica gel with acetone/hexane, 860 mg of 3,3-ethylenedioxy11β-(4-methoxyphenyl)-9-estrene[17(β-1')spiro-3']oxiran-5α-ol is obtained, mp 98° C. (with decomposition.

EXAMPLE 12

Under argon, 3 g of tert-butylmethyl sulfoxide in 35 ml of absolute tetrahydrofuran is combined dropwise at 0° C. with 15.6 ml of a 1.6-molar n-butyllithium solution in hexane. The reaction mixture is then combined dropwise with a solution of 4.6 g of 11β-(4-dimethylaminophenyl)-3,3-ethylenedioxy-9-estrene[17(β-1')spiro-3']oxiran-5α-ol in 30 ml of tetrahydrofuran. The mixture is agitated for 10 hours at room temperature, then stirred into ice/water, and extracted with ethyl acetate. The solution is washed with water and dried over sodium sulfate. Chromatography on silica gel is used to isolate 3.9 g of 11β-(4-dimethylaminophenyl)-21-(1,1-dimethylethylsulfinyl)-3,3-ethylenedioxy-19-nor-17α-pregn-9-ene-5α,17β-diol as a mixture of diastereomers, with acetone/hexane; the product is obtained as a solid foam.

EXAMPLE 13

Analogously to Example 12, 3.6 g of 3,3-ethylenedioxy-11β-(4-methoxyphenyl)-9-estrene[17(β-1')spiro-3']-oxiran-5α-ol is reacted with tert-butylmethyl sulfoxide to produce 21-(1,1-dimethylethylsulfinyl)-3,3-ethylenedioxy-11β-(4-methoxyphenyl)-19-nor-17α-pregn-9-ene-5α,17β-diol as a mixture of diastereomers. After chromatography on silica gel with acetone/hexane, 2.3 g of a solid foam is thus obtained.

EXAMPLE 14

1.8 g of 11β-(4-dimethylaminophenyl)-21-(1,1-dimethylethylsulfinyl)-3,3-ethylenedioxy-19-nor-17α-pregn-9-ene-5α, 17β-diol (as a mixture of diastereomers) is agitated in 50 ml of glacial acetic acid and 20 ml of water for 20 hours at room temperature, thus obtaining 1.1 g of 11β-(4-dimethylaminophenyl)-21-(1,1-dimethylethylsulfinyl)-17β-hydroxy-19-nor-17α-pregna-4,9-dien-3-one as a mixture of diastereomers, obtained as a solid foam.

EXAMPLE 15

Analogously to Example 14, 2.1 g of 21-(1,1-dimethylethylsulfinyl)-3,3-ethylenedioxy-11β-(4-methoxyphenyl)-19-nor-17α-pregn-9-ene-5α,17β-diol (mixture of diastereomers) is reacted with aqueous glacial acetic acid to 21-(1,1-dimethylethylsulfinyl)-17β-hydroxy-11β-(4-methoxyphenyl)-19-nor-17α-pregna-4,9-dien-3-one (mixture of diastereomers), producing 1.3 g of a foamy product.

EXAMPLE 16

1.6 g of 11β-(4-dimethylaminophenyl)-21-(1,1-dimethylethylsulfinyl)-17β-hydroxy-19-nor-17α-pregna-4,9-dien-3-one (mixture of diastereomers) is stirred in 30 ml of tetrahydrofuran and 10 ml of water at room temperature with 520 mg of N-chlorosuccinimide. After 2 hours, the mixture is diluted with ethyl acetate, washed repeatedly with water, and dried over sodium sulfate. Chromatography of the crude product on silica gel with acetone/hexane yields 420 mg of 11β-(4-dimethylaminophenyl)-3-oxo-4,9-estradiene[17(β-1')-spiro-5'][1,2]oxathiolane-2'-oxide, mp 98° C.

EXAMPLE 17

Analogously to Example 16, 1.3 g of 21-(1,1-dimethylethylsulfinyl)-17β-hydroxy-11β-(4-methoxyphenyl)-19-nor-17α-pregna-4,9-dien-3-one (mixture of diastereomers) is reacted with N-chlorosuccinimide. Chromatography on silica gel with acetone/hexane produces, as a mixture of diastereomers, 180 mg of 11β-(4-methoxyphenyl)-3-oxo-4,9-estradiene[17(β-1')spiro-5'][1,2]oxathiolane-2'-oxide, mp 95° C., and 390 mg of 11β-(3-chloro-4-methoxyphenyl)-3-oxo-4,9-estradiene[17(β-1')spiro-5'][1,2]oxathiolane-2'-oxide as a solid foam.

EXAMPLE 18

(a) 1.5 g of 11β-(4-dimethylaminophenyl)-3,3-ethylenedioxy-9-estrene[17(β-1')spiro-3']oxiran-5α-ol is combined with 140 mg of p-toluenesulfonic acid and 5 ml of liquid methylamine and heated in a steel vessel for 17 hours at an oil bath temperature of 130° C. After cooling and opening of the bomb tube, excess methylamine is evaporated after transfer into a crystallizing dish. The residue is taken up in methylene chloride, washed neutral with water, and concentrated after drying over sodium sulfate, yielding 1.7 g of 11β-(4-dimethylaminophenyl)-3,3-ethylenedioxy-17α-methylaminomethyl-9-estrene-5α,17β-diol as the crude product.

(b) A solution of 1.6 g of 11β-(4-dimethylaminophenyl)-3,3-ethylenedioxy-17α-methylaminomethyl-9-estrene-5α,17β-diol and 800 mg of potassium tert-butylate in 10 ml of carbonic acid dimethyl ester is heated under reflux for 45 minutes. After cooling, the mixture is diluted with methylene chloride, washed neutral with water, dried over sodium sulfate, and concentrated to dryness under vacuum. The crude product is purified on 135 g of silica gel with a hexane-acetone gradient (0–60% acetone), thus isolating 650 mg of 11β-dimethylaminophenyl)-3,3-ethylenedioxy-3'-methyl-4,9-estradiene[17(β-1')spiro-5']oxazolidin-2'-one, mp 228°–229° C. $[\alpha]_D^{25} = +101.5°$.

EXAMPLE 19

490 mg of 11β-(4-dimethylaminophenyl)-3,3-ethylenedioxy-3'-methyl-4,9-estradiene [17(β-1')spiro-5']oxazolidin-2'-one is agitated for 20 hours at room temperature in 13.7 ml of glacial acetic acid and 5.3 ml of water. The mixture is poured on ice/water, adjusted with potassium hydroxide (solid) to be slightly alkaline, filtered off, and the residue taken up in methylene chloride. The organic solution is concentrated after having been washed neutral and dried, thus isolating, after chromatography on silica gel with hexane/acetone, 430 mg of 11β-(4-dimethylaminophenyl)-3'-methyl-4,9-estradiene[17(β-1')spiro-5']oxazolidine-2',3-dione as a foamy product.

EXAMPLE 20

Under argon, a mixture of 2.8 g of 3,3-ethylenedioxy-11β-(4-methoxyphenyl)-9-estrene[17(β-1')spiro-3']-oxiran-5α-ol, 8.4 g of N-methylurethane, and 0.7 g of potassium tert-butylate is agitated in 20 ml of hexamethylphosphoric triamide at 130° C. for 4 hours. The mixture is then poured on ice/water and the thus-separated, oily product is extracted with methylene chloride. The organic extracts are washed with water, dried, and evaporated, thus isolating as a solid foam 710 mg of 3,3-ethylenedioxy-5α-hydroxy-11β-(4-methoxyphenyl)-3'-methyl-9-estrene[17(β-1')spiro-5']-oxazolidin-2'-one.

EXAMPLE 21

Under the conditions of Example 19, 600 mg of the foamy product obtained in Example 20 is reacted with 70% aqueous acetic acid, worked up, and purified, thus obtaining 260 mg of 11β-(4-methoxyphenyl)-3'-methyl-4,9-estradiene-[17(β-1')spiro-5']oxazolidine-2',3-dione as an amorphous solid.

EXAMPLE 22

10.5 g of 3,3-ethylenedioxy-11β-(4-methoxyphenyl)-9-estrene[17(β-1')spiro-3']oxiran-5α-ol is combined with 1.05 g of p-toluenesulfonic acid and 35 ml of liquid methylamine and heated in a steel vessel for 16 hours to 130° C. oil bath temperature. After cooling and opening of the bomb tube, excess methylamine is removed by evaporation and the residue is transferred to a filter. The mixture is washed neutral with water, the crude product is taken up in ethyl acetate, filtered off, and the filtrate, concentrated to one-fourth its volume, is combined with hexane, thus obtaining 3.8 g of 3,3-ethylenedioxy-11β-(4-methoxyphenyl)-17α-methylaminomethyl-9-estrene-5α,17β-diol as an amorphous compound, which latter is dissolved in 30 ml of trimethylamine. At 5° C., 3 ml of thionyl chloride is added dropwise thereto, the reaction mixture is stirred for 30 minutes, and then poured into ice/water. The mixture is extracted with ethyl acetate, washed with water, and dried over sodium sulfate. The resultant crude product is stirred in 40 ml of 70% acetic acid for 3 hours at 60° C. and then worked up as described in Example 19, thus isolating 900 mg of 11β-(4-methoxyphenyl)-3'-methyl-3-oxo-4,9-estradiene[17(β-1')spiro-5'][1,2,3]oxathiazolidine-2'-oxide (as a mixture of diastereomers) in the form of a foamy product.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An 11β-aryl estradiene of Formula I

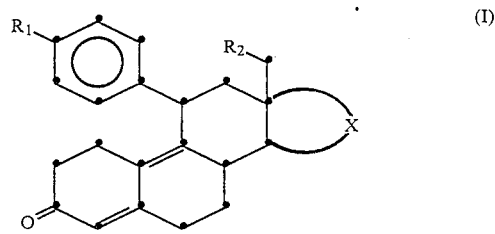

wherein $R_1$ is

wherein $R^I$ and $R^{II}$ each independently is alkyl of 1–4 carbon atoms, or $R^I$ and $R^{II}$ together with the connecting N-atom form a 5- or 6-membered hererocyclic ring whose remaining atoms are all C-atoms, or which also includes an additional N-atom, an additional O or S atom or a combination thereof;

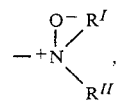

wherein $R^I$ and $R^{II}$ are as defined above; —$SR^{III}$, wherein $R^{III}$ is methyl, ethyl or phenyl; or —$OR^{IV}$, wherein $R^{IV}$ is methyl, ethyl, propyl, methoxymethyl, allyl, or β-dimethylaminoethyl; $R_2$ is hydrogen, methyl, or ethyl;

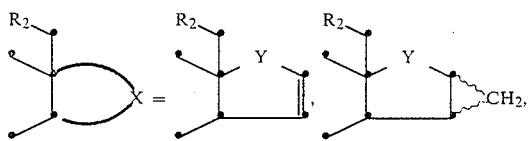

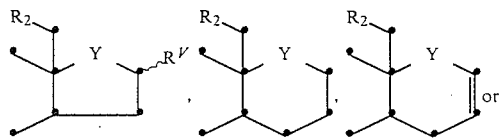

wherein the wavy lines ⁓⁓⁓ mean that the substituent is in the α- or β-position, and

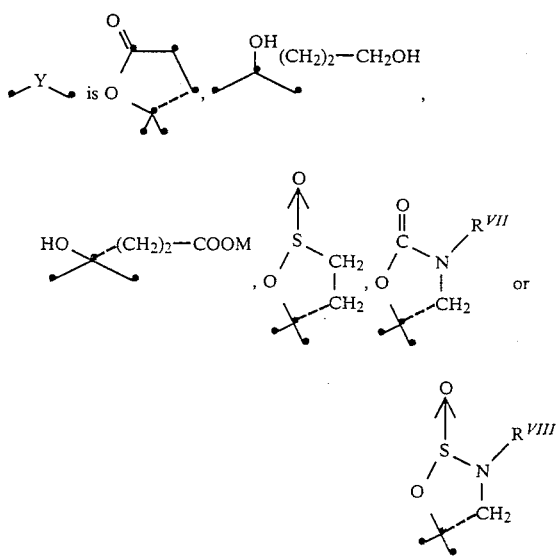

M is Na, K or Li; and $R^V$, $R^{VI}$, $R^{VII}$ and $R^{VIII}$ each independently is alkyl of 1–4 carbon atoms.

2. A lactone or potassium salt of 3-[11β-(4-dimethylaminophenyl)-17β-hydroxy-3-oxo-4,9(10)-estradien-17α-yl]propionic acid, a compound of claim 1.

3. 11β-(4-Dimethylaminophenyl)-17β-hydroxy-17α-(3-hydroxypropyl)-4,9(10)-estradien-3-one, a compound of claim 1.

4. A lactone or potassium salt of 3-[11β-[4-(2-dimethylaminoethoxy)phenyl]-17β-hydroxy-18-methyl-3-oxo-4,9(10)-estradien-17α-yl]propionic acid, a compound of claim 1.

5. 11β-[4-(2-Dimethylaminoethoxy)phenyl]-17β-hydroxy-17α-(3-hydroxypropyl)-18-methyl-4,9(10)-estradien-3-one, a compound of claim 1.

6. A lactone or sodium salt of 3-[17β-hydroxy-11β-(4-methoxyphenyl)-3oxo-4,9(10)-estradien-17α-yl]propionic acid, a compound of claim 1.

7. 17β-Hydroxy-17α-(3-hydroxypropyl)-11β-(4-methoxyphenyl)-4,9(10)-estradien-3-one, a compound of claim 1.

8. 11β-(4-Dimethylaminophenyl)-17β-hydroxy-17α-(3-hydroxypropyl)-16β-methyl-4,9(10)-estradien-3-one, a compound of claim 1.

9. 11β-(4-Dimethylaminophenyl)-17β-hydroxy-17α-(3-hydroxypropyl)-18 -methyl-4,9(10)-estradien-3 one, a compound of claim 1.

10. 11β-(4-Dimethylaminophenyl)-17aβ-hydroxy-17aα-(3-hydroxypropyl)-D-homo-4,9(10)-estradien-3-one, a compound of claim 1.

11. 11β-[4-(2,5-Dimethylpyrrol-1-yl)phenyl]-17β-hydroxy-17α-(3-hydroxypropyl)-4,9(10)-estradien-3-one, a compound of claim 1.

12. 17β-Hydroxy-17α-(3-hydroxypropyl)-11β-(4-piperidinophenyl)-4,9(10)-estradien-3-one, a compound of claim 1.

13. 17β-Hydroxy-17α-(3-hydroxypropyl)-11β-[4-(pyrrolidin-1-yl)phenyl]-4,9(10)-estradien-3-one, a compound of claim 1.

14. 11β-(4-Dimethylaminophenyl)-3-oxo-4,9-estradiene [17(β-1′)spiro-5′][1,2]oxathiolane-2′oxide, a compound of claim 1.

15. 11β-(4-Methoxyphenyl)-3-oxo-4,9-estradiene [17(β-1′)spiro-5′][1,2]oxathiolane-2′-oxide, a compound of claim 1.

16. 11β-(4-Dimethylaminophenyl)-3′-methyl-4,9-estradien-[17(β-1′)spiro-5′]oxazolidine-2′,3-dione, a compound of claim 1.

17. 11β-(4-Methoxyphenyl)-3′-methyl-4,9-estradiene-[17(β-1′)spiro-5′]oxazolidine-2′,3-dione, a compound of claim 1.

18. 11β-(4-Methoxyphenyl)-3′-methyl-3-oxo-4,9-estradiene [17(β-1′)spiro-5′][1,2,3]oxathiazolidine-2′-oxide, a compound of claim 1.

19. A compound of claim 1 wherein $R_1$ is

20. A compound of claim 1 wherein $R_1$ is dimethylamino.

21. A compound of claim 1 wherein $R_1$ is alkoxy.

22. A compound of claim 1 wherein $R_1$ is methoxy.

23. A pharmaceutical composition comprising an amount of a compound of claim 1 effective to cause an abortion and a pharmaceutically acceptable carrier.

24. A pharmaceutical composition comprising 10–1000 mg of a compound of claim 1 and a pharmaceutically acceptable carrier.

25. A method inducing an abortion in a patient comprising administering to the patient an effective amount of a compound of claim 1.

26. A method of treating a patient suffering from aldosteronism comprising administering to the patient an effective amount of a compound of claim 1.

* * * * *